US005670145A

United States Patent [19]
Wright

[11] Patent Number: 5,670,145
[45] Date of Patent: Sep. 23, 1997

[54] BIOLOGICALLY ACTIVE SYSTEM FOR DISPERSION OF PHEROMONES

[75] Inventor: James E. Wright, Cave Creek, Ariz.

[73] Assignee: Troy Biosciences, Inc., Phoenix, Ariz.

[21] Appl. No.: 593,576

[22] Filed: Jan. 30, 1996

[51] Int. Cl.$^6$ ............ A01N 25/02; A01N 37/06; A01N 63/04

[52] U.S. Cl. ............ 424/84; 424/93.5; 54/546; 54/772.3

[58] Field of Search ............ 424/84, 405, 407, 424/93.5; 514/772.3, 546

[56] References Cited

U.S. PATENT DOCUMENTS

| | | | |
|---|---|---|---|
| 2,800,457 | 7/1957 | Green et al. | 512/4 |
| 2,800,458 | 7/1957 | Green | 428/402.2 |
| 3,577,515 | 5/1971 | Vandegaer | 424/497 |
| 4,017,030 | 4/1977 | Coplan et al. | 239/44 |
| 4,237,113 | 12/1980 | Cardarelli | 514/86 |
| 4,456,587 | 6/1984 | Keith | 424/84 |
| 4,830,860 | 5/1989 | Ranade | 424/486 |
| 4,834,745 | 5/1989 | Ogawa et al. | 604/890.1 |
| 4,923,119 | 5/1990 | Yamamoto et al. | 424/84 |
| 5,135,744 | 8/1992 | Alexander et al. | 424/84 |
| 5,503,839 | 4/1996 | Saguchi et al. | 424/408 |

OTHER PUBLICATIONS

S.M. El-Fateh et al., "Large Scale Evaluation of Phermones in Reducing the Population Density of the Pink Bollworm, *Pectinophora gossypiella* (Saunders)," Bull Ent. Soc. Egypt, Econ., Ser. 17, 1988/1989, pp. 19–28.

H. M. Flint et al., "Aerial Concentration of Gossyplure, the Sex Phermone of the Pink Bollworm (Lepidoptera: Gelechiidae), in Cotton Field Treated with Long-Lasting Dispensers," Environmental Entomology, vol. 19, No. 6, Dec. 1990, pp. 1845–1851.

*Primary Examiner*—John Pak
*Attorney, Agent, or Firm*—Banner & Witcoff, Ltd.

[57] ABSTRACT

The present invention relates to liquid formulations containing pheromones, in particular sex pheromones of insects, as an active ingredient, supported by an inert liquid material whereby a film-forming resin is formed on the surface of the liquid material when exposed to oxygen. The liquid pheromone formulations may be sprayed onto the leaves of plants and cured in situ on the leaves. The cured pheromone formulation is capable of controlled release of the pheromone over a period of time.

15 Claims, 6 Drawing Sheets

Mean Number of Pectinophora gossypiella Per Trap Per Observation

* Entire area oversprayed with insecticide
INVENTIVE COMPOSITION was applied on 9/3

BIOLOGICALLY ACTIVE SYSTEM FOR DISPERSION OF PHEROMONES

The present invention relates to liquid formulations containing pheromones, in particular sex pheromones of insects, as an active ingredient, supported by an inert liquid material whereby a film-forming resin is formed on the surface of the liquid material when exposed to oxygen. The liquid pheromone formulations may be sprayed onto the leaves of plants and cured in situ on the leaves. The cured pheromone formulation is capable of controlled release of the pheromone over a period of time.

BACKGROUND OF THE INVENTION

Insects severely damage crops all over the world. For example, pink bollworm (*Pectinophora gossypiella* Saunders) is the most damaging pest of Egypt's most important crop, cotton (*Gossypium barbadense* L.) This pest is also common in other areas that grow cotton. The development of resistance to insecticides by intensive insecticide applications has made pink bollworm control with conventional measures more difficult in recent years. Such intensive applications not only place a greater economic burden on growers, but also diminish populations of beneficial insects. The result is often outbreaks of secondary pests and further insecticide use.

Alternatives to insecticide use has been studied for many years. One alternative is the use of pheromones. Pheromones are chemicals which are secreted outside the body of insects and may be classified into different classes depending on the type of behavioral reaction they induce, e.g., aggregation, sexual, trail and alarm pheromones. Sex pheromones are usually secreted by the females to attract males for mating.

If pheromones are dispersed on leaves of a crop plant, in small quantities over a continuous period of time, pheromone thresholds are created that modify an insect's behavior, disrupting mating and thus impacting the reproductive processes in the insects. Mating is reduced which results in insect control in the area in which the pheromone threshold is maintained.

Gossyplure has been found to be effective in preventing mating in pink bollworm and, consequently, reducing the number of insecticide treatments necessary. El-Fateh et al., "Large scale evaluation of pheromone in reducing the population densities of the pink bollworm," *Bull. Ent. Soc. Egypt, Eco. Ser.,* 17 (1989) demonstrated that two gossyplure formulations significantly reduced numbers of male moths caught in monitoring traps. Flint et at., "Aerial concentrations of gossyplure, the sex pheromone of pink bollworm (Lepidoptera: Geleclidae), in cotton fields treated with lasting dispensers," Environ. *Entomol. V.,* 19(6): 1845–1851 (1990) found that numbers of male moths caught in pheromone-baited traps were reduced up to 100% for up to 60 days following treatments. Subsequent work verified that gossyplure applications can significantly prevent pink bollworm mating and provide economic control (Douglass et al, "Four-year study of pink bollworm (*Pectinophora gossypiella* (Saunders) control using commercial gossyplure products to prevent mating," *International Cotton Pest Work Committee, Mazatlan,* Mexico, 1992).

Thus, the use of gossyplure is a viable alternative to control pink bollworm. Fewer insecticide applications are required, beneficial insects can be preserved, risks to humans and the environment can be minimized, and overall insect control costs may be lowered. However, gossyplure applied alone or in simple solvent systems is not an effective means to release the gossyplure since it does not remain on the cotton leaves for a sufficient amount of time to be effective in the control of the pink bollworm. Further, gossyplure is photosensitive and is destroyed at a faster than usual rate by UV light. Thus, means to release the pheromone in controlled manner is necessary.

Controlled-release gossyplure dispensers have been used, but these must be tied to the cotton plant and are labor intensive and extremely time consuming, for example, taking up to one hour per acre for one man to apply. Further, the dispensers are often left in the fields and may foul up harvesting equipment or become incorporated in the picked cotton and foul equipment in the gin. U.S. Pat. Nos. 4,834,745, 4,923,119 and 4,830,860 provide examples of dispensers.

An alternative to gossyplure dispensers are slow-release formulation systems containing pheromones. Examples of such systems are aqueous suspensions of pheromone-containing micro-capsules having walls made of polyamides (U.S. Pat. No. 3,577,515) or of gelation (U.S. Pat. Nos. 2,800,457 and 2,800,458); multi-layer polymeric systems consisting of capillaries with an open end (A.C.S., 1976, page 283) and hollow fiber systems consisting of capillaries with an open end through which the pheromone volatilizes (U.S. Pat. Nos. 4,017,030). These systems require a sophisticated technique for their preparation and distribution in the field. The release kinetics of the pheromone in these systems is not linear due to the structure of the capsules which is a disadvantage.

Another alternative is spraying a liquid polymeric composition onto the leaves of plants. For example, U.S. Pat. No. 4,456,587 describes an aqueous mixture capable of being sprayed on to leaves of plants and being cured in situ on the leaves. The cured mixture comprises polyvinylalcohol and polyvinylpyrrolidone.

SUMMARY OF THE INVENTION

An objective of the present invention is to provide an inert liquid formulation for the controlled release of a pheromone, over an extended period of time.

Another objective of the present invention is to provide a liquid formulation which can be easily applied to plant material by spraying or other means.

Another objective of the present material is to provide a liquid formulation which will cure in situ on the plant material.

A further objective of the present invention is to provide a safe, effective means to control insects by creating disruption of the mating of insects.

A further objective of the present invention is to provide an economical means to control insects, particularly insects harmful to cotton plants.

The present invention is directed to a liquid formulation for spraying onto the leaves of plants comprising an amount of pheromone effective to control insects, a mixture of copolymers of vinyl-ethylene with vinyl acetate and butylphthalate and a solvent. Upon exposure to oxygen, the liquid formulation reacts to form a permeable resin layer which slowly releases the pheromone into the environemt.

BRIEF DESCRIPTION OF THE DRAWINGS

FIG. 1 shows counts of pink bollworm moths in seventeen fields treated with the inventive composition.

FIG. 2 shows counts of pink bollworm moths in seven fields treated with the inventive composition.

FIG. 3 shows counts of pink bollworm moths.

DETAILED DESCRIPTION OF THE INVENTION

Figure 1:
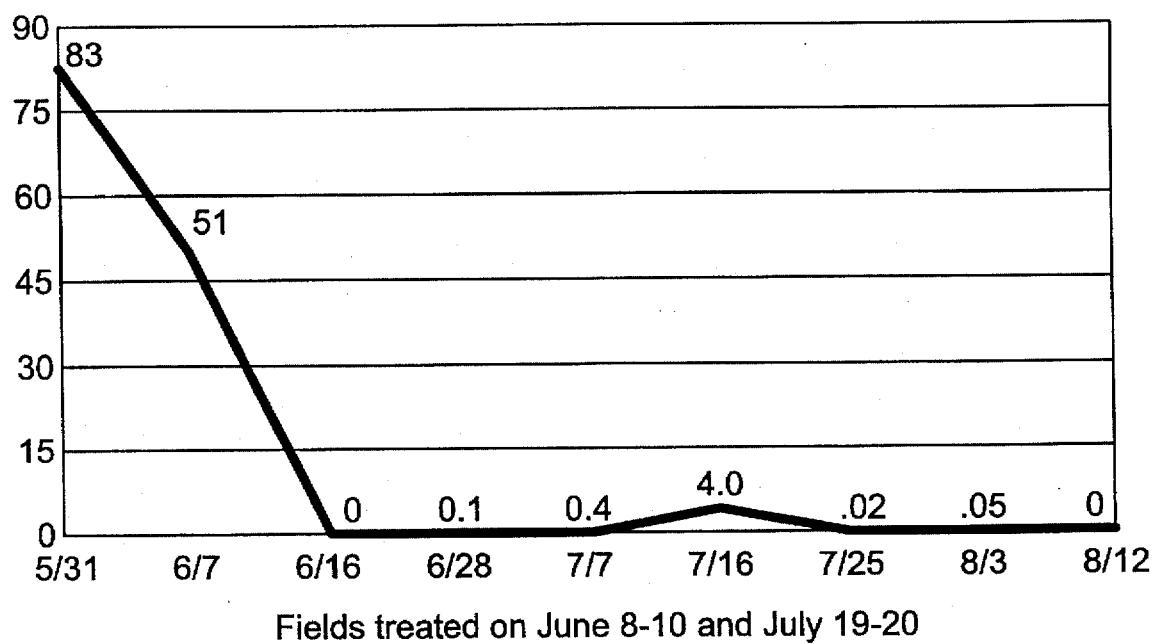

The present invention relates to liquid formulations containing pheromones as active ingredients for insect control. The pheromones are supported by an inert liquid material comprising a mixture of copolymers of vinyl-ethylene with vinyl acetate and butylphthalate and a solvent. When the liquid material is exposed to oxygen, a permeable resin film is formed on its surface. This film allows for slow release of the pheromone into the environment.

The liquid pheromone formulations of the present invention can be sprayed onto the leaves of plants and cured in situ on the leaves. The cured pheromone formulation is capable of controlled release of the pheromone over a period of time.

In accordance with the present invention, the mixture of copolymers of vinyl-ethylene with vinyl acetate and butylphthalate is mixed with a solvent to form a copolymer matrix. The pheromone is incorporated into this preformed copolymer matrix and bonded via covalent or ionic bonds to the copolymer matrix which allows for uniform and continuous release of the pheromone from the surface of a copolymer matrix. The controlled release of a pheromone is achieved by the permeation-moderated transfer of the pheromone from the copolymer matrix through the matrix surface while maintaining a predetermined concentration or emission level for a specified period of time.

An important advantage of the present invention is that the pheromone undergoes minimal biochemical degradation in the copolymer matrix.

A liquid formulation in accordance with the present invention comprises an amount of pheromone effective to control insects; a mixture of copolymers of vinyl-ethylene with vinyl acetate and butylphthalate; and a solvent whereby a resin film is formed on the surface of the liquid formulation when exposed to oxygen.

The pheromone is present in amounts effective for insect control, such as an amount effective to disrupt the mating of the insects, and typically is between about 5 and 25 wt %, preferably between about 8% and 15 wt %. A specific embodiment of the present invention contains about 11% of a pheromone.

The mixture of copolymers of vinyl-ethylene with vinyl acetate and butylphthalate is present in amounts and proportions sufficient to form an appropriate copolymer matrix. The liquid formulation contains between about 60 and 90 wt %, preferably between about 70 and 85 wt %, of a mixture of copolymers. A specific embodiment of the present invention contains about 78 wt % of the copolymers. The ratio of vinyl ethylene to acetate to butylphthalate can vary from 10 to 60%, depending on the desired characteristics of the copolymer, but must provide a copolymer which will form a resin film upon exposure to oxygen (air). Suitable copolymer matrix mixtures may be obtained from, for example, KOLLANT in Italy under the product name ARBOKOL.

The solvent is present in amounts to disperse the pheromone into the copolymer. The formulation contains between about 5 and 20 wt %, more preferably between about 8 and 15 wt % of the solvent. A specific embodiment of the present invention contains about 11 wt % of the solvent.

Any pheromone effective for insect control can be used in the liquid formulation of the present invention. Pheromones may be used for mating disruption or for detection of insect populations. Examples of such pheromones include codling moth, *Cydia(Laspeyresia)pomonella*, diamondback moth, *Plutella xylostella*, oriental fruit moth, *Grapholitha molestra*, peach twig borer, ,*Anarsia lineatella*, pink bollworm, *Pectinophora gossypiella*, spiny bollworm, tomato pinworm, etc. The preferred pheromone for pink bollworm is gossyplure. Gossyplure, for example is available as 92% Tech.

The solvent is compatible with the copolymer and aids in dispersing the pheromone into the copolymer. Examples of solvents include propylene glycol, ethyl acetate, dichloromethane, petroleum ether, hexane, glycerol, and methyl ethyl ketone. Preferably, the solvent is propylene glycol.

Generally, the pheromones are not water soluble and may be diluted with propylene glycol, for example. This is done when mixing the formulation under a blanket of nitrogen. An example is equal amounts of propylene glycol plus pheromone (wt/wt basis) is then added under the blanket of nitrogen at a ratio of 15 to 30 wt % of the pheromone/propylene glycol to that of the matrix. The matrix is sealed from air and, when opened, is applied directly as such with no further dilutions. It may be possible to apply the matrix mechanically, using pressure application equipment in large areas.

The desired rate of release of the pheromone and the duration may be achieved by adjusting the proportions of the copolymer, solvent and pheromone.

A protective sunscreen may be included in amounts of about 0.01 to 1% of the composition. Other ingredients that may be included in the liquid formation are feeding substrates such as sugar (about 1% to 5% by weight).

Chemical insecticides or insect specific fungi may also be added for additional insect control.

Water is present in the polymer matrix in amounts between 40–55% by weight. Additional water, up to 10–15% by weight may be added to reduce the viscosity. The amount of water contained in the initial polymer mixture depends upon the total spray to be applied per unit area and the dilution rate to be used and is within the skill of the art.

The liquid formulation of the present invention is produced by mixing together the mixture of copolymers of vinyl ethylene with vinyl-acetate, butylphthalate, and the solvent and then adding the pheromone. The liquid formulation may be cured by elevating the incubation temperature to 40° C. or is cured in situ after sprayed on foliage. The elevated temperature generates a phenomenon termed "blooming". The color of the matrix changes from a semi-liquid grey matrix to a black soft elastic semi-solid. The elastic semi-solid matrix provides a diffusion-dissolution or migration release mechanism for the pheromone to release from the copolymer, which allows an extremely long release duration of the pheromone.

The liquid formulation of the present invention may be applied to leaves of plants by any means within the skill of the art. Preferably the liquid formulation is applied by spraying. Prior to application, the liquid formulation may be diluted to any suitable and effective concentration.

In general, the final product is a non-inflammable, semi-solid which is dark grey in color. The solids content is 50–60%, and the viscosity is 9.0–10.0 cps at 20° C. The specific weight at 20° C. is 1.03 kg/dm³ and the pH is 5.5–6.0. The minimum temperature to film is at 20° C. for one hour. The product is neither toxic nor harmful; however, in case of contact with the skin, it should be washed thoroughly with water.

EXAMPLES

Release Rate of Gossyplure Under Laboratory Conditions

Example 1

The release effect of a gossyplure formulation was measured in response to temperature elevation over an interval of time measured in days. The formulation used in the release project:

| | |
|---|---|
| Copolymer | 78% |
| Propylene Glycol | 11% |
| Gossyplure 92% Tech | 11% |

The formulation concentration of the Batch assayed was 10.1% w/w of gossyplure. Multiple one gram samples were used to study the release rate of the gossyplure. The one gram samples were weighed on an aluminum weigh boat and placed in an oven at a constant temperature of 40° C. (+/–3) for incubation. Recording of oven temperature was measured on a daily time interval.

At a time interval of 10 days for the first 60 days, a one gram sample was assayed by gas chromatography (GC) to determine the w/w percent concentration of the gossyplure remaining in the sample.

Prior to the samples being assayed, the excess aluminum weigh boat was removed by cutting around the sample and then the one gram sample was extracted in 25 ml of methylene chloride (DCM) with one ml of internal standard (ISTD) added. The sample was placed in the 25 ml of DCM with one ml of ISTD, and then placed on the orbital shaker for 30 minutes. After the sample was extracted, 2 µl of the extract was injected on the GC three times and quantitated for the percent level of gossyplure present in the sample. Randomly two one-gram samples, instead of one sample, were assayed on the same day. The extract was quantified by injecting three standards of known concentration of gossyplure with a known concentration level of Internal Standard Methyl Hepta-decanoate.

After noticing a dramatic increase in the level of gossyplure during the first ten day interval, a second group of one-gram samples of the present invention was placed in the oven for incubation and assayed on a daily time interval for twelve days to determine the slope of the baseline during the twelve day period. Validation of the extraction and analysis procedure was confirmed by assaying samples that were spiked with a known concentration of gossyplure and assayed on the same day of an incubated one-gram sample.

This study successfully tested the release rate of gossyplure formulations under laboratory conditions. The emission ram over a 103 days of incubation time averaged 0.68 mg/day at 40° C. Parameters that were also used to determine any chemical changes were pH and % moisture. The pH remained constant at 5.62 (+/–0.4). The % moisture decreased during incubation time from 43% to 30.7%. A grey matrix color indicated high moisture level. A black color indicated low moisture level.

The pheromone solution contained a vinyl ethylene-acetate-butylphthalate copolymer, propylene glycol, and (ZZ)-7, (Z,E)-11-Hexadecadien-1-ol, acetate whereby a 1:1 mixture of the (Z,Z) and (Z,E) isomers was present. The appearance was a gray semi-solid pasty fluid having an acetic odor and a pH of 5.6. The solidification point was greater than 12° C., and the % moisture was 30–35.

Field Tests of Gossyplure Formulations

Example 2

A liquid, polymeric controlled-release and UV-shielded formulation, made in accordance with claim 1 and containing 22 g of gossyplure per 150 ml of product, was tested in field trials performed in Monofia and Bene Suef governorates in Egypt and at Aguila and Cibola, Ariz. The objective was to assess the efficacy of applications of the invention by pump-applied controlled-release gossyplure in the suppression of pink bollworm (*Petinophora gossypiella* Saunders) in Pima cotton (*Gossypium barbadense* L.)

The formulation in accordance with the present invention was applied manually in UV-shielded, controlled-release drops with a hand-operated pump dispenser, using a rapid application mode of three to four acres per hour.

Egypt

In early studies in Egypt by other researchers, pink bollworm control was achieved with three successive gossyplure applications and only two sprays of conventional insecticide (Moawad et al, "Mating disruptions as a method of control for *Pectinophora gossypiella* (Saunders) in Middle Egypt" 4th Arab Cong. of Plant Protection, Cairo, 1–5 Dec. 1991). The study was repeated in 1992 on a larger scale. An area of 6722 ha. was treated with gossyplure-impregnated polyethylene rope in El-Minia governorate. Bollworm control was compared with other areas treated with conventional insecticides. The study showed significant reduction in male moths caught per trap and decreased boll infestation compared to insecticide treated areas. The number of insecticide applications necessary for control of pink bollworm was reduced 50% to 75% in the pheromone-treated areas (Moawad et al, "Male Disruption pheromone as a new strategy in controlling pink bollworm," *Pectinophora gossypiella* (Saunders), in Egypt. Proc 1994 Beltwide Cotton Conf. National Cotton Council of America. pp. 1035–1038).

Field trials were established in Egypt in small (<15 feddans) fields and moderate-sized (>30 feddans) fields in the Ganzour-Berket-Elsabar Markoz of the Monofia governorate and in moderate-sized fields (16–55 feddans) in the Beni Menen-El Fashy Markaz of the Bene Suef-Governorate. The formulation was applied at the full rate in early June and again at a half rate in mid-July with a 150 ml hand pump at the rate of approximately 0.5 grams of formulated gossyplure product per drop. The formulation was in the form of a thick polymeric liquid which provides a UV-shielded, controlled-release matrix. The drop dried within an hour of application. The invention was applied to mature leaves in the upper 25% of the plant canopy. The first treatment on June 8–10 was applied at 300 sites per feddan or about one 0.5 gram pump per 150 square feet. That is, one pump per 5 paces (17 feet) down a cotton row, and continuing down every third row across the field. The second treatment on Jul. 19–20 was applied to only 150 sites per feddan at a half rate. Fields were treated at the rate of 3–4 acres per hour per man.

Pheromone traps monitored adult pink bollworm activity before and after the applications. Male moths captured in each trap were counted and removed every three days. Following applications, trap numbers were increased to insure more accurate counts. Boll samples were selected at random weekly, July through August, at the rate of 100 bolls per sample and were assayed to determine % infestation.

The Monofia governorate insecticide-treated comparison fields were treated four times by air with half-rate conventional insecticides:

| Application | Date | Insecticide Used |
| --- | --- | --- |
| 1st | 7/09–16 | (Mixtures) - Cutabron (0.3751) - Deenette (0.51) |
| 2nd | 7/24–8/3 | (Pyrethroids) - Pestox (0.081) - Baythroid (0.3751) |
| 3rd | 8/15–24 | (O-P. comb) - Dursban (0.51) - Cyanox (0.51) - Curacron (0.751) |
| 4th | 8/30–9/7 | (Carbamates) - Larvin (37.5% @ 0.51) |

The invention treated fields were treated with only single-chemistry insecticides at half rates on Jul. 27, Aug. 3, Aug. 16–20 and Sep. 1–3. Not all fields were treated each time and each field received a total of only three treatments, a considerable economic savings.

The Bene Suef governorate comparison fields were treated by air with half rate Kindo insecticide when boll infestation reached 5% in mid-July. Treatments continued at two week intervals for a total of three to four applications. The invention treated fields were also treated with half-rate insecticides (Kindo, Deenette, and Cyanox) when the infestation exceeded 5%. Of the seven fields, one received two insecticide applications and the other received three. Thus, one to two insecticide applications were saved.

Arizona

Two trials were established in Phoenix, Ariz. A four-acre test plot in Aguila, Arizona and a three-acre test plot in Cibola, Ariz. were treated on Sep. 3 and Aug. 26, respectively. The procedures used in the trials in Egypt were utilized: 300 deposits (150 ml) of the invention per acre were deposited in the upper 25% of the canopy, one deposit every 17 feet and on every third row across the field.

The application was quick and easy to use, allowing one man to treat at least three acres an hour. A single application of the invention was made.

Results

Trap Counts

Figure 2:
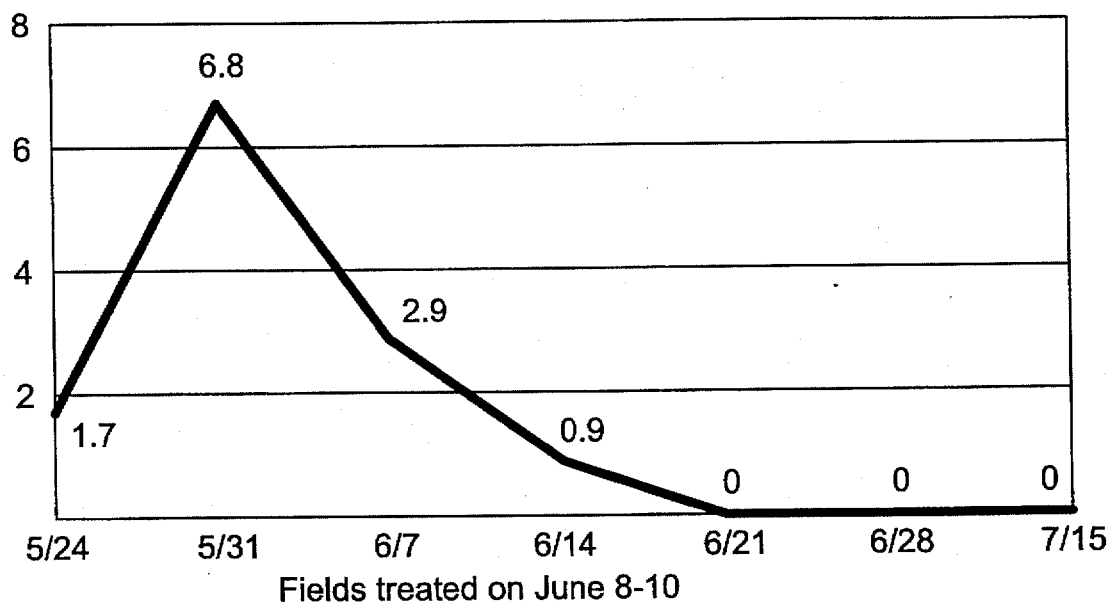
Figure 3:
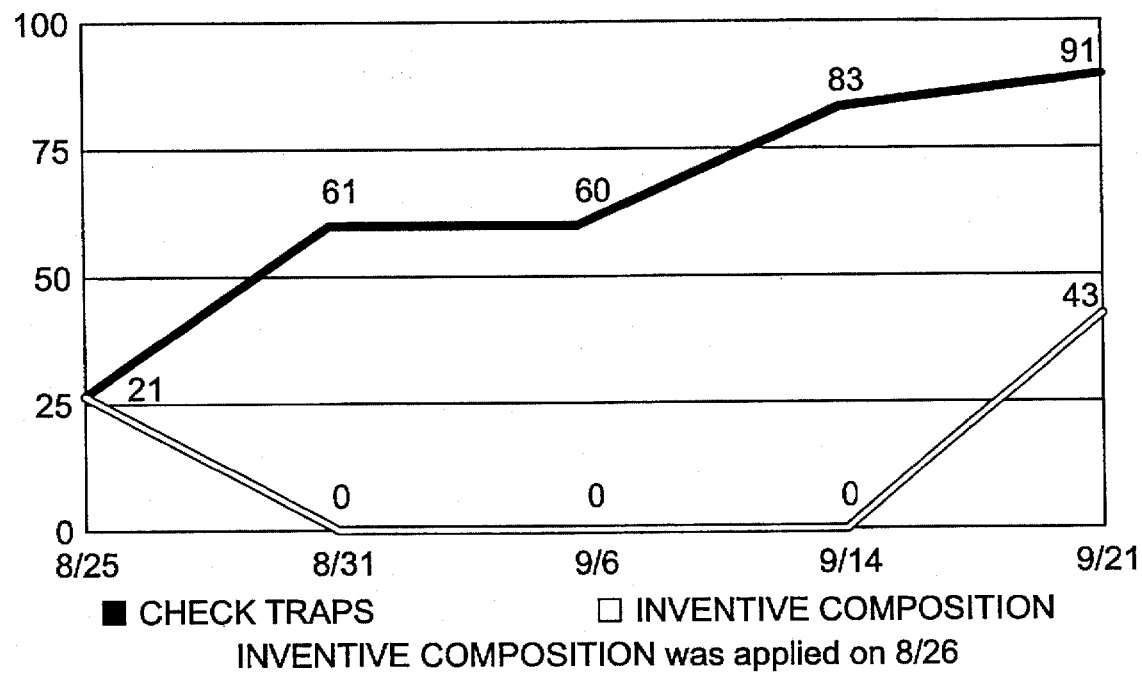
Figure 4:
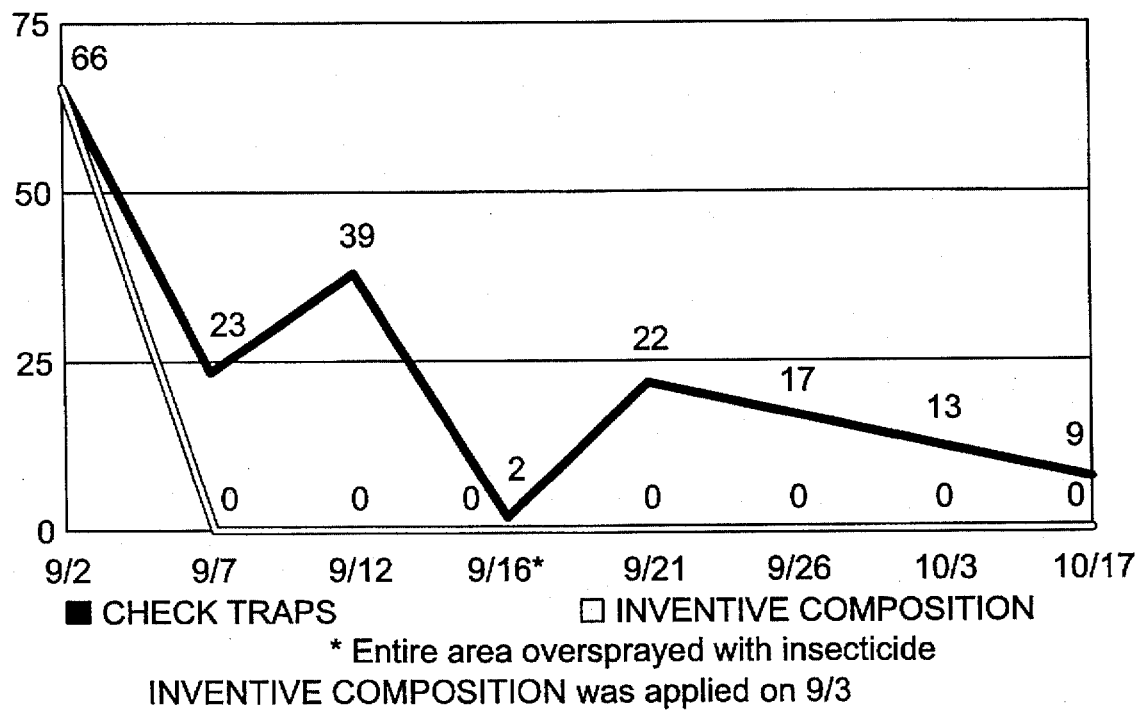
FIG. 4 shows counts of pink bollworm moths.

Trap counts were reduced to zero levels immediately following application of the formulation of the invention in both Egypt and Arizona trials. Numbers of male moths trapped remained at or near zero for 30 to 45 days (Tables 1 and 2, FIGS. 1 and 2) in the Egyptian trials. Arizona trials showed the same pattern. Comparisons with check traps are shown in FIG. 3 and 4.

High temperatures during these trials ranged from 34° C. to 42° C., at Cibola, temperatures were in excess of 38° C. for 22 days and over 40° C. for 12 days. At Aguila, daytime highs averaged 39° C. Since pheromone release continued for nearly 4 weeks at Cibola and for 45 days at Aguila under these conditions, high temperature provides no impediment to the controlled release.

Numbers of Infested Bolls

Figure 5:
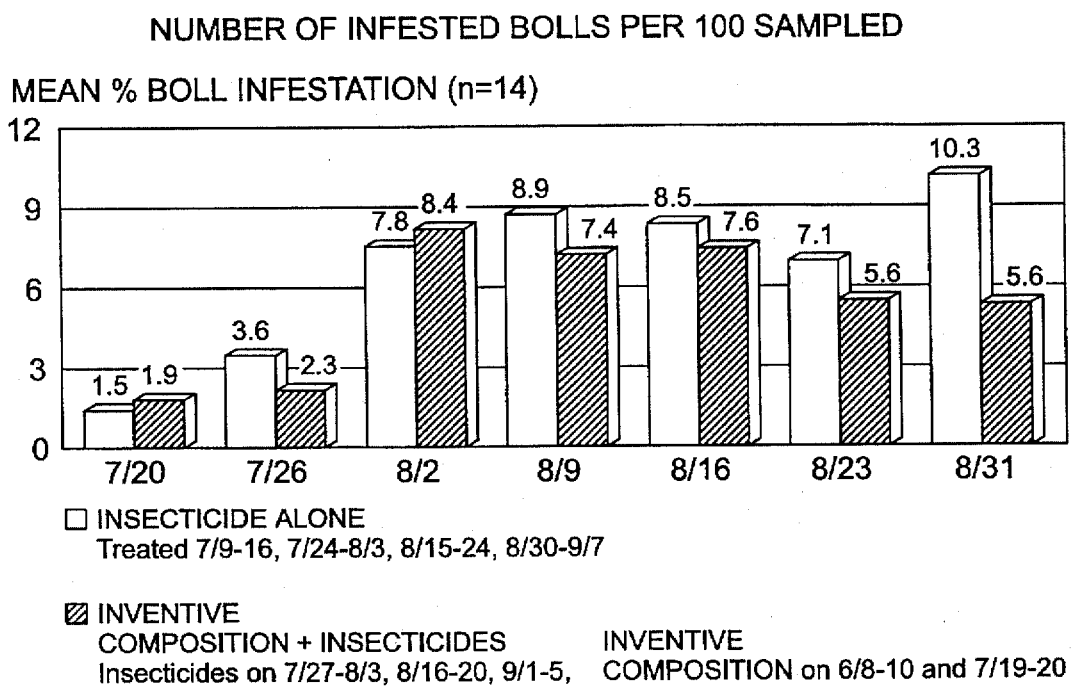
FIG. 5 shows control of pink bollworm with the inventive formulation with insecticides compared to insecticides alone.
Figure 6:
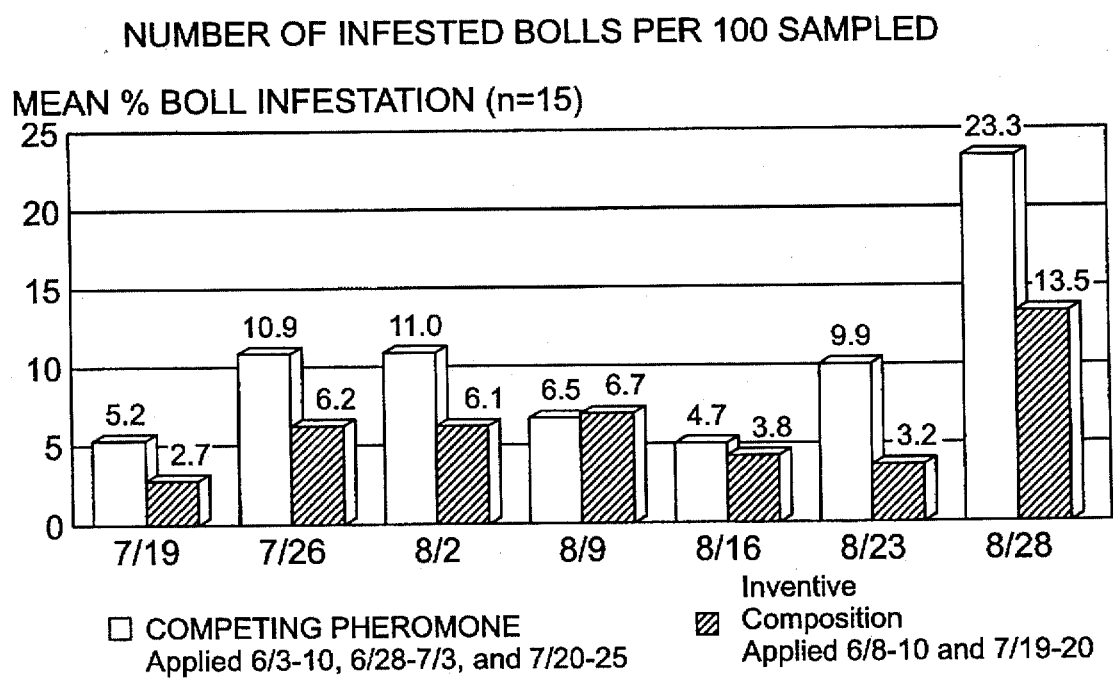
FIG. 6 shows control of pink bollworm with mating disruption pheromones.

The percent of bollworm infested bolls from the various Egyptian test localities are shown in Table 3 and FIGS. 5 and 6. Fields treated with the invention required 25% to 50% fewer insecticide treatments and had lower levels of infestation than fields treated with insecticides or the other pheromone product. In addition, larger fields had lower levels of damaged bolls and a more uniform level of mating disruption due to minimization of wind and perimeter (untreated field) effects (Table 3).

These trials demonstrated the practicality of pink bollworm control with simple and labor intensive application equipment. However mating disruption can be maximized and boll damage and pesticide use further minimized by successive applications of the invention. Furthermore, large areas may be treated quickly and uniformly with aircraft or mechanized equipment.

Equipment can be modified for this purpose to apply the invention for low-impact insect biocontrol over large areas.

TABLE 1

Counts of Pink Bollworm Moths in Seventeen Fields Treated With The Inventive Compositon
Mean Number of *Pectinophora gossypiella* Per Trap Per Week.

| FIELD # | AREA (Feddans) | 5/31 | 6/7 | 6/16 | 6/28 | 7/7 | 7/16 | 7/25 | 8/3 | 8/12 |
| --- | --- | --- | --- | --- | --- | --- | --- | --- | --- | --- |
| 31 | 13 | 30 | 58 | 0 | 0 | 2 | 22 | 20 | 0 | 3 |
| 17 | 14 | — | — | 0 | 0 | 1 | 7 | 7 | 0 | 1 |
| 18 | 15 | 104 | 62 | 0 | 0 | 2 | 48 | 38 | 0 | 0 |
| 40 | 30 | 176 | 49 | 0 | 1 | 3 | 13 | 7 | 0 | 0 |
| 2, 8 | 40 | 55 | 26 | 0 | 1 | 3 | 18 | 12 | 1 | 2 |
| 1, 2 | 52 | 79 | 39 | 0 | 1 | 2 | 13 | 8 | 0 | 0 |
| 3, 4, 5 | 47 | 136 | 120 | 0 | 1 | 3 | 15 | 23 | 1 | 1 |
| | Total = | 580 | 354 | 0 | 4 | 16 | 143 | 115 | 2 | 7 |
| | # Traps = | 7 | 7 | 39 | 39 | 39 | 39 | 39 | 39 | 39 |
| | x̄ = | 83.0 | 51.0 | 0 | 0.1 | 0.4 | 4.0 | 0.02 | 0.05 | 0.2 |

Fields treated on June 8–10 and July 19–20

TABLE 2

Counts of Pink Bollworm Moths in Seven Fields Treated With The Inventive Composition
Mean Number of *Pectinophora gossypiella* Per Trap Per Week

| AREA (FEDDANS) | 5/24 | 5/31 | 6/7 | 6/14 | 6/21 | 6/28 | 7/5 | 7/15 |
| --- | --- | --- | --- | --- | --- | --- | --- | --- |
| 55 (4) | 10 | 16 | 2 | 1 | 0 | 0 | 0 | 0 |
| 30 (2) | 0 | 35 | 9 | 2 | 0 | 0 | 0 | 0 |
| 45 (4) | 8 | 9 | 5 | 3 | 0 | 0 | 0 | 0 |
| 16 (1) | 0 | 9 | 13 | 3 | 0 | 0 | 0 | 0 |
| 25 (2) | 5 | 10 | 5 | 2 | 0 | 0 | 0 | 0 |
| 30 (1) | 3 | 17 | 2 | 1 | 0 | 0 | 0 | 0 |

TABLE 2-continued

Counts of Pink Bollworm Moths in Seven Fields
Treated With The Inventive Composition
Mean Number of *Pectinophora gossypiella* Per Trap Per Week

| AREA (FEDDANS) | 5/24 | 5/31 | 6/7 | 6/14 | 6/21 | 6/28 | 7/5 | 7/15 |
|---|---|---|---|---|---|---|---|---|
| 20 (1) | 0 | 6 | 8 | 2 | 0 | 0 | 0 | 0 |
| Total = | 26 | 102 | 44 | 14 | 0 | 0 | 0 | 0 |
| $\bar{x}$ = | 1.7 | 6.8 | 2.9 | 0.9 | 0 | 0 | 0 | 0 |

Fields Treated on June 8–10
( ) = Number of traps per field

TABLE 3

The Effect Of The Inventive Composition On
Pink Bollworm Infestation
NUMBER AND PERCENT OF INFESTED BOLLS PER 100 SAMPLED

| PLOT | FIELD NO. | AREA (Fed) | 7/20 | 7/26 | 8/2 | 8/9 | 8/16 | 8/23 | 8/31 |
|---|---|---|---|---|---|---|---|---|---|
| El Amra | 31 | 13 | 4 | 5 | 24 | 33 | 23 | 16 | 6 |
| Kasaly Om Elwan | 17 | 14 | 1 | 8 | 12 | 3 | 2 | 3 | 13 |
| Ware El Gesr | 18 | 15 | 1 | 16 | 22 | 24 | 6 | 12 | 10 |
| El Maktaa Gharby | 6 | 11 | 3 | 2 | 5 | 10 | 6 | 6 | 9 |
| Small Field Means | | | 2.25% | 7.75% | 15.75% | 17.50% | 9.25% | 9.25% | 9.50% |
| | 40 | | 0 | 1 | 7 | 13 | 11 | 6 | 6 |
| Baraket | 41 | 30 | 0 | 1 | 7 | 16 | 12 | 9 | 2 |
| Abou El-Nour | 42 | | 3 | 2 | 6 | 12 | 21 | 7 | 5 |
| | 7 | | 2 | 0 | 10 | 5 | 7 | 2 | 5 |
| El Sharwa | 8 | 40 | 2 | 7 | 14 | 8 | 8 | 6 | 4 |
| Near Babel | 9 | | 1 | 1 | 4 | 6 | 3 | 2 | 6 |
| | 10 | | 3 | 3 | 7 | 6 | 8 | 6 | 4 |
| | 1 | | 1 | 2 | 8 | 5 | 3 | 5 | 4 |
| Maktaa | 2 | 52 | 1 | 2 | 14 | 6 | 3 | 6 | 7 |
| Khashaba | 11 | | 3 | 2 | 6 | 6 | 7 | 4 | 9 |
| | 12 | | 2 | 4 | 7 | 1 | 5 | 3 | 6 |
| | 3 | | 0 | 2 | 12 | 4 | 6 | 13 | 9 |
| El Khabba | 4 | 47 | 4 | 2 | 5 | 8 | 8 | 4 | 5 |
| El Tawela | 5 | | 5 | 3 | 11 | 8 | 4 | 5 | 5 |
| Large Field Means | | | 1.90% | 2.28% | 8.40% | 7.42% | 7.57% | 5.57% | 5.57% |
| Insecticide Field Means | | | 1.54% | 3.60% | 7.80% | 8.90% | 8.50% | 7.10% | 10.30% |

I claim:

1. A liquid formation for spraying onto the leaves of plants comprising an amount of pheromone effective to control insects; a mixture of copolymers of vinyl-ethylene with vinyl acetate and butylphthalate, and a solvent; whereby a film is formed on the surface of the liquid formulation when exposed to oxygen.

2. The liquid formulation of claim 1 comprising between about 60 and 90 wt % of the copolymer.

3. The liquid formulation of claim 1 comprising between about 5 and 20 wt % of the solvent.

4. The liquid formulation of claim 1 comprising between about 5 and 25 wt % of the pheromone.

5. The liquid formulation of claim 1 wherein the pheromone is gossyplure.

6. The liquid formulation of claim 1 wherein the solvent is selected from the group consisting of propylene glycol, ethylacetate, dichloromethane, petroleum ether, hexane, glycerol, and methyl ethyl ketone.

7. The liquid formulation of claim 6 wherein the solvent is propylene glycol.

8. The liquid formulation of claim 1 further comprising a chemical insecticide or insect specific fungi.

9. A liquid formulation for spraying onto leaves of plants comprising between about 5 and to 25 wt % of a pheromone; between about 60 and 90 wt % of a mixture of copolymers of vinyl-ethylene with vinyl acetate and butylphthalate; and between about 5 to 20 wt % of a solvent.

10. The liquid formulation of claim 9 wherein the pheromone is gossyplure.

11. The liquid formulation of claim 9 wherein the solvent is selected from the group consisting of propylene glycol, ethylacetate, dichloromethane, petroleum ether, hexane, glycerol, and methyl ethyl ketone.

12. The liquid formulation of claim 11 wherein the solvent is propylene glycol.

13. A method of controlling insects comprising applying a liquid formulation onto leaves of plants, the liquid formulation comprising an amount of pheromone effective to control insects; a mixture of copolymers of vinyl-ethylene with vinyl acetate and butylphthalate; and a solvent; whereby a film is formed on the surface of the liquid formulation when exposed to oxygen.

14. The method of claim 13 further comprising diluting the liquid formulation with water prior to applying.

15. The method of claim 13 applying the liquid formulation by spraying.

* * * * *